United States Patent [19]

Reich et al.

[11] Patent Number: 4,651,568

[45] Date of Patent: Mar. 24, 1987

[54] GLASS BOTTLE INSPECTION

[75] Inventors: Frederich R. Reich; Errol V. Allen, both of Richland, Wash.

[73] Assignee: Kirin Beer Kabushiki Kaisha, Tokyo, Japan

[21] Appl. No.: 646,893

[22] Filed: Aug. 30, 1984

[51] Int. Cl.[4] .......................................... G01N 29/04
[52] U.S. Cl. ..................................... 73/612; 73/622; 73/644
[58] Field of Search ................. 73/600, 609, 610, 612, 73/622, 628, 629, 644, 640; 209/590

[56] References Cited

U.S. PATENT DOCUMENTS

| 2,795,133 | 6/1957 | Ots | 73/600 |
| 3,375,706 | 4/1968 | Pandelis et al. | 73/644 |
| 4,065,960 | 1/1978 | Grabendorfer et al. | 73/609 |
| 4,217,782 | 8/1980 | Pont | 73/638 |

OTHER PUBLICATIONS

J. Krauthramer et al., *Ultrasonic Testing of Materials*, Springer-Verlag, N.Y., 1983, pp. 332-337 and 439-443.

Primary Examiner—Michael J. Tokar
Assistant Examiner—John E. Chapman, Jr.
Attorney, Agent, or Firm—Koda & Androlia

[57] ABSTRACT

In glass bottle inspection, a pulse of acoustic wave is injected into a portion of the glass bottle forming a closed path for the propagation of the acoustic wave pulse so that the injected acoustic wave pulse travels round the closed plath, and acoustic wave pulse is detected while it is travelling round the closed path. Whether there is a defect along the closed path is judged in accordance with the magnitude of the detected acoustic wave pulse.

4 Claims, 17 Drawing Figures

LONGITUDINAL

FIG. 2(b)

SHEAR

GLASS BOTTLE INSPECTION

BACKGROUND OF THE INVENTION

The present invention relates to a method and system for inspecting a glass bottle such as that for containing food or beverage.

A crack or chip defect which can be produced at any point in the production cycle or use lifetime is of concern as it can impact the quality of the container product and consumer appeal. Bottle defects can normally be detected using optical techniques based on the principles of scatter, refraction or absorption, but the detection sensitivity is a strong function of defect size and its orientation and location within the bottle. A small crack which extends radially outward in the bottle is especially difficult to detect because it provides a very small cross-section area when viewed at the angle where light will enter or pass through the bottle wall.

SUMMARY OF THE INVENTION

An object of the invention is to provide a method and a system capable of detecting those kinds of defects, e.g., a crack extending radially outward, which are difficult to detect by an optical system.

According to one aspect of the invention, there is provided a method for inspecting a glass bottle comprising the steps of:

injecting a pulse of acoustic wave into a portion of the glass bottle forming a closed path for the propagation of the acoustic wave pulse so that the injected acoustic wave pulse travels round the closed path, detecting the acoustic wave pulse while the acoustic wave pulse is travelling round the closed path, and judging whether there is a defect along the closed path in accordance with the magnitude of the acoustic wave pulse.

According to another aspect of the invention, there is provided a system for inspecting a glass bottle comprising:

means for injecting a pulse of acoustic wave into a portion of the glass bottle forming a closed path for the propagation of the acoustic wave pulse so that the injected acoustic wave pulse travels round the closed path, means for detecting the acoustic wave pulse while the acoustic wave pulse is travelling round the closed path, and means for judging whether there is a defect along the closed path in accordance with the magnitude of the acoustic wave pulse.

The disclosed technique is especially useful with glass containers but its potential application field is not limited by the container shape (round, oval or square). It is especially useful on container areas where the surface structure (such as threads on the bottle mouth), surface texture (embossing and painted labels), and container opacity (doped glass, etc.) severely limit the passage of optical energies which would normally be used to indicate the presence of a defect.

DESCRIPTION OF THE PREFERRED EMBODIMENTS

BASIC ACOUSTIC PRINCIPLES

Although the analogies between optical and acoustical are rich, there are some basic principles in acoustics that have no optical equivalent. In order to make this disclosure more understandable, a few of these properties will be discussed below.

An acoustic wave is a propagating mechanical perturbation and thus requires that the propagating media possess a suitable, continuous elasticity. The acoustic propagation is dependent on both the physical nature of the acoustic wave and on the elasticity properties of this host material. However, it is the material properties that produce the characteristic phenomena that are important and allow the use of acoustic energy to be used for defect inspection. The magnitude of the acoustic energy transmitted across a boundary is dependent on the acoustic impedance (product of the material's density and acoustic velocity) match of the materials at the boundary. Reference should be made, in this connection, to Flugge, S., ed. 1962. Encyclopedia of Physics, Volume XI/2 Acoustics II. Springer-Verlag OHG/Berlin, Gottingen Heidelberg, and Hueter, T. F. and R. H. Bolt. 1955. Sonics. John Wiley and Sons, Inc., New York, N.Y.

Acoustic energy will be reflected at interfaces where the acoustic impedances are not equal. In order to inject acoustic energy into a container (such as a glass bottle), the acoustic impedance differences between the acoustic energy source and the container must be small as a large impedance difference will cause most of the acoustic energy to be reflected at the boundary surface. The propagation direction of the acoustic energy after it crosses the boundary depends on the relative acoustic velocities of the two materials forming the boundary. The incident and reflected energy on each side of the boundary will have the same but opposite angle with respect to the boundary normal. The energy crossing the boundary will follow an acoustic version of Snell's law $$\phi_{Li} = \phi_{Lr} \quad (1)$$

$$\frac{\sin\phi_{Li}}{C_{L1}} = \frac{\sin\phi_{Lt}}{C_{L2}} = \frac{\sin\phi_{Sr}}{C_{S1}} = \frac{\sin\phi_{St}}{C_{S2}} \quad (2)$$

where $C_L$ and $C_S$ are longitudinal and shear wave velocities and i, t and r refer to the incident, transmitted and reflected acoustic energy. From the prospective we are pursuing in the disclosure, this law indicates that acoustic energy crossing a boundary can change its propagation direction as well as its basic form (i.e., longitudinal to shear or vice versa). The acoustic path between the acoustic source (or detector) and the container is therefore a very important element in the application of acoustic energy for defect inspection.

Figure 1:
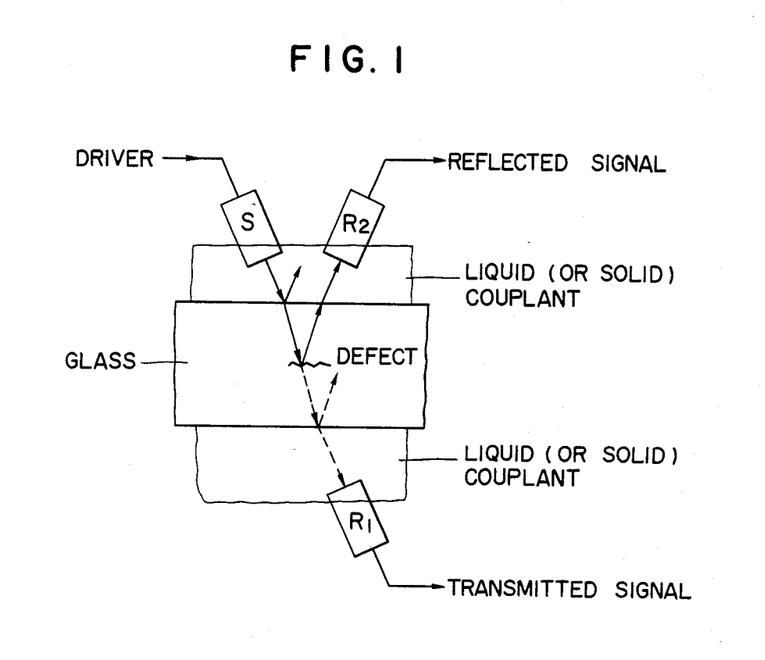
FIG. 1 is a schematic diagram showing principle of injection and detection of an acoustic wave for the purpose of defect detection.

A container crack or chip produces a discontinuity within the normally consistent container wall. This discontinuity affects the normal propagation of acoustic energy which then can be detected and used to indicate the presence of the defect as illustrated in FIG. 1. The acoustic energy is coupled into the glass via the liquid (or solid) coupling material from the acoustic source S. Some of this energy will be reflected (the magnitude depends on the acoustic impedance match at the boundary) at the boundaries, but most of the energy would reach the receiver $R_1$. The discontinuity produced by a defect will redirect or reflect some of the acoustic energy which may be detected by the second receiver $R_2$. Thus, we could either monitor $R_1$ (through transmission) for a loss of signal or $R_2$ (pulse echo) for the presence of a signal to detect the presence of a defect.

Since the acoustic wave properties depend on the elasticity of a media, any discontinuity will affect the acoustic transmission and will provide an internal boundary where the energy can be scattered or reflected. An internal crack in the path of the acoustic wave will reflect or scatter some of the acoustic energy. It is these acoustic properties that allow acoustic techniques to be used in sensing defects in the mouth, neck, wall and bottom areas of beverage and food containers.

Figure 2A:
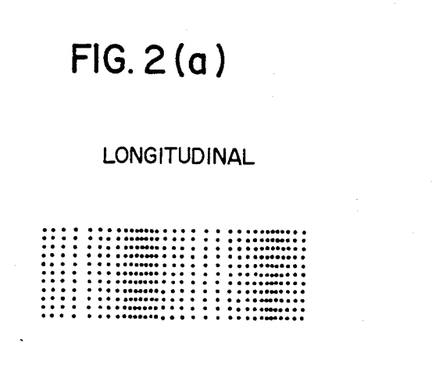
FIGS. 2(a) and 2(b) are diagrams illustrating the distinction between the longitudinal wave and the shear wave.
Figure 2B:
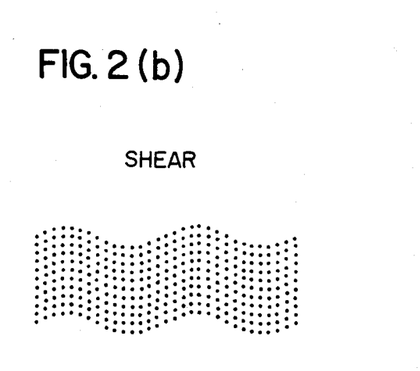

The two fundamental types of acoustical waves, longitudinal and transverse, are shown in FIG. 2. The longitudinal and transverse labels (FIGS. 2(a) and 2(b)) refer to the direction of the movement of the material particles relative to the propagation direction of the mechanical perturbation or acoustic wave. It is obvious that the acoustic waves interacting with the defect illustrated in FIG. 1 may be either longitudinal or shear waves or a combination of both. For defect inspection, the important issues are the ability to generate and detect acoustic energy which has a high probability of interacting with a defect or of being modified due to the presence of a defect condition. It has however been found that transverse waves are advantageous in that it is easier to inject into a bottle mouth and derive from the bottle mouth.

CONTAINER INSPECTION CONCEPTS

The subject of this disclosure is the application of acoustic pulse-echo and through transmission techniques for detecting defects in product containers and particularly in glass food and beverage containers. Glass containers are of specific interest, since large volumes are used by the food, beverage and chemical or pharmaceutical industries. Acoustic inspection particularly lends itself to the inspection or detection of cracks in glass containers as these defects produce a large perturbation of the normally uniform acoustic properties. The symmetry of the container will also allow a large container area to be inspected with a small number of acoustic source and receiver transducers.

THROUGH TRANSMISSION INSPECTION

Figure 3:
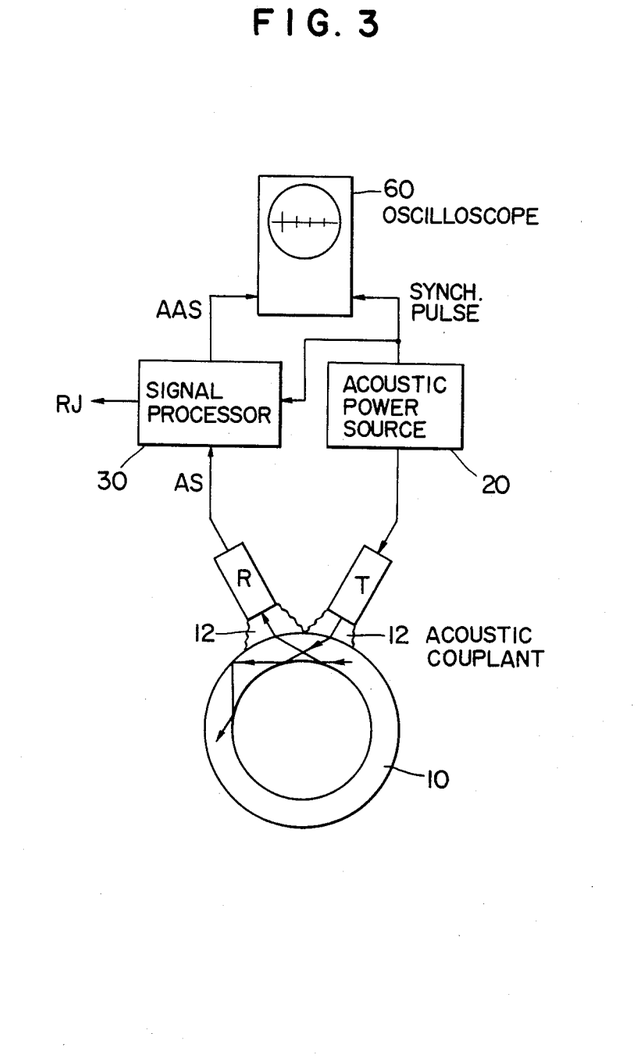
FIG. 3 is a schematic diagram showing an example of arrangement for through transmission inspection.
Figure 4:
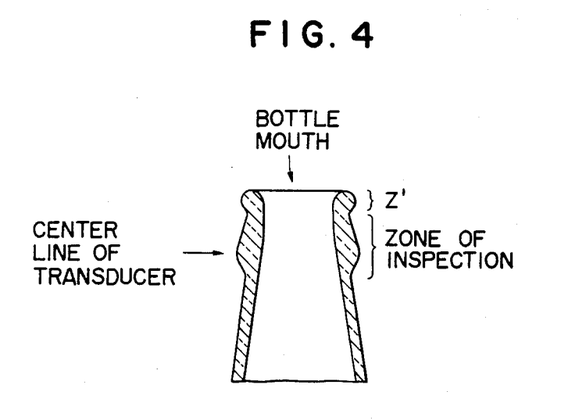
FIG. 4 is a sectional view showing a bottle mouth.

A typical setup for through transmission inspection of a container segment, which forms an embodiment of the invention, is illustrated in FIG. 3. The acoustic energy from the source transducer (electro-acoustic transducer) T is injected through a couplant 12 into the container wall and will propagate around the bottle wall 10 until this energy is dissipated. FIG. 4 shows an example of zone of a bottle to be inspected and a preferred alignment of the center line of the transducer, which is at the top (where the tangent line is parallel to the axis of the bottle) of the convexity of the cross section.

Figure 5:
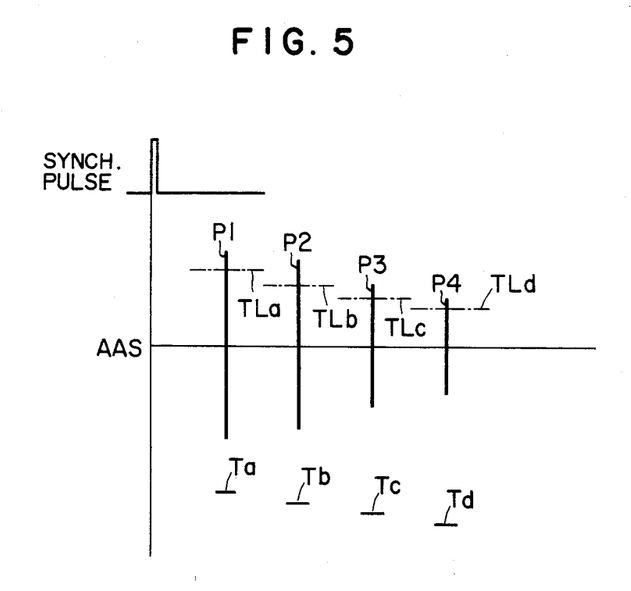
FIG. 5 is a diagram showing the threshold levels of the respective threshold detectors and the time intervals of the respective timing gates.

By choosing acoustic frequencies that have a low absorption loss in the container materials, this acoustic wave will make several revolutions around the container wall until it is not detectable with the receiving transducer R. With each pass around the container wall, the receiver transducer (an electro-acoustic transducer) R will tap off some of this acoustic energy. The integrity of the acoustic path around the circumference of the container can then be assessed from any one of the received pulses or from all of them. As an example, typical receiver signals for acoustic energy inspection in a good bottle mouth area are shown in FIG. 5. The acoustic source transducer T is electronically pulsed by an acoustic power source 20 so it emits a short acoustic wave which then propagates around the circumference of the bottle mouth. Pulses derived by tapping off or detecting the acoustic energy upon first, second, third . . . full round trips are indicated by P1, P2, P3, . . . respectively in FIG. 5. With no defect present, we should expect to see the same signal pattern (amplitude and time distribution) as that shown in FIG. 5. The time to circle a bottle and the low attenuation in the bottle would allow us to use the signal processing technique which can be implemented by a signal processor 30 illustrated in FIG. 6. In the system illustrated in FIG. 6, the pulses derived upon up to fourth round trip are utilized and processed.

Figure 6:
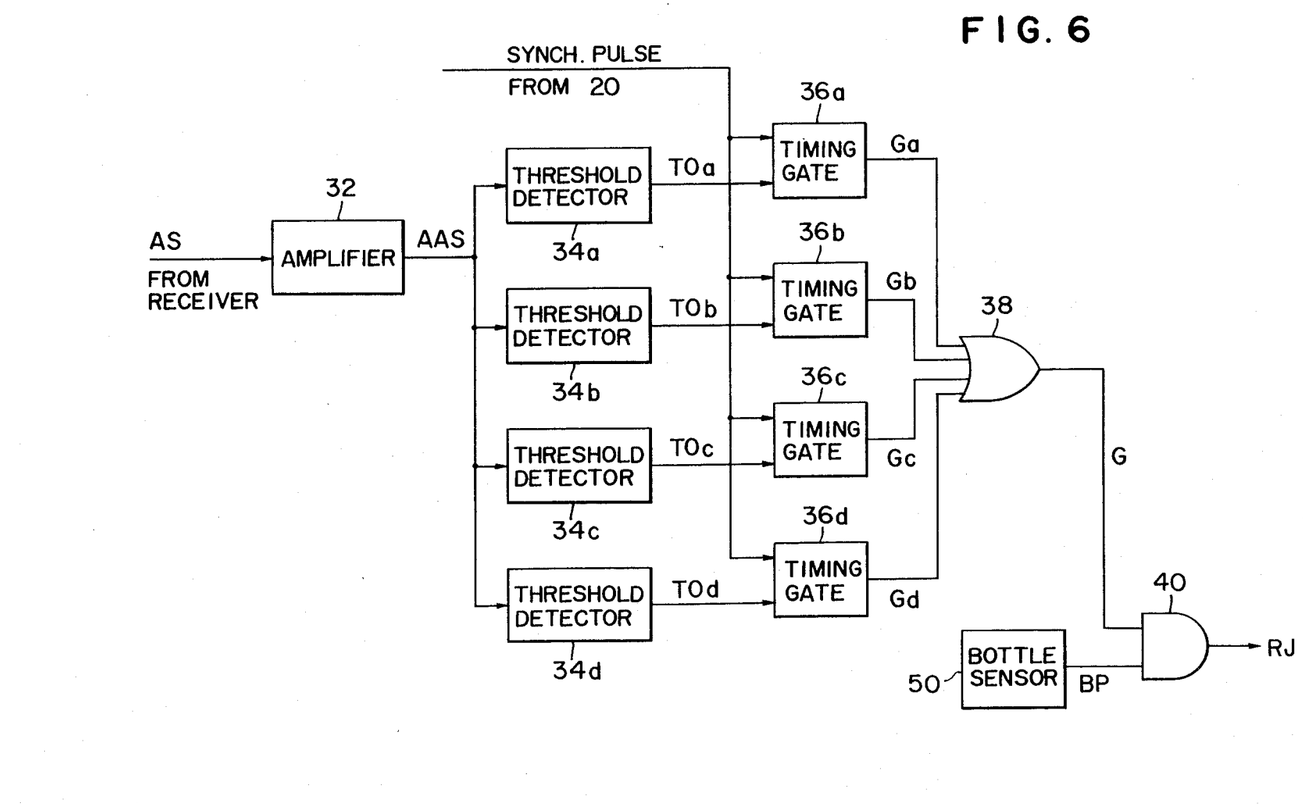
FIG. 6 is a block diagram showing an example of a signal processor 30 of FIG. 3.

An amplifier 32 amplifies the output, i.e., acoustic signal AS from the receiver to produce an amplified acoustic signal AAS.

Threshold detectors $34a$-$34d$ receive the amplified acoustic signal AAS. The outputs $TO_a$-$TO_d$ of the threshold detectors $34a$-$34d$ are at high or logical "1" level when the signal AAS is not above the respective predetermined threshold levels $TL_a$-$TL_d$ (FIG. 5).

Timing gates $36a$-$36d$ are provided in association with the respective threshold detectors $34a$-$34d$, and define respective time intervals $T_a$-$T_d$ (FIG. 5) responsive to a synchronous signal produced by the acoustic pulse source 20 in synchromism with the injection of the acoustic wave pulse. The time intervals $T_a$-$T_d$ are so chosen that the pulses derived upon the first to fourth round trips is normally (i.e., if there is no defect) expected to appear within the respective time intervals $T_a$-$T_d$. Each timing gate is formed to produce a signal ($G_a$- $G_d$) of "1" if the associated threshold detector does not find the amplified acoustic signal AAS to have exceeded the threshold level during the defined time interval.

The threshold levels $TL_a$-$TL_d$ of the threshold detectors 34a-34d are so chosen that the pulse which is normally expected to appear during the time intervals $T_a$-$T_d$ which is defined by the associated timing gates 36a-36d. The travelling acoustic wave pulse attenuates gradually, so that the threshold detectors 34a-34d associated with the timing gates 36a-36d which open later have lower threshold levels $TL_a$-$TL_d$.

Thus the combination of the threshold detectors 34a-34d and the timing gates 36a-36b functions to compare the amplified acoustic signal AAS with a threshold level which tends to be decreased with time.

An OR gate 38 is provided to receive the outputs $G_a$-$G_d$ of the timing gates 36a-36d, and an AND gate 40 is provided to receive the output G of the OR gate and a bottle present signal BP from a bottle sensor 50. The bottle sensor 50 senses the presence of the bottle at the inspection position at which the bottle is in alignment with the acoustic transmitter and receiver unit, and its output, the bottle present signal BP is at "1" when the bottle is sensed.

The output $G_a$-$G_d$ of "1" will pass the OR gate 38, and will pass the AND gate 40 provided that the AND gate is opened by the bottle present signal BP, to render the reject signal RJ "1" thereby indicating that the bottle in the inspection position has a defect.

With the circuit arrangement of FIG. 6, a defect is recognized if any of the acoustic signals derived upon the first to fourth round trips is below the respective threshold levels. But the arrangement may alternatively be such that a defect is recognized if the acoustic signal is found to be below the respective threshold levels at a plurality of (e.g., two) threshold detectors.

The acoustic pulse may be produced several times while the bottle is in the inspection position. Although an advantage of the acoustic inspection according to the invention is that the entire circumference of the bottle mouth can be uniformly inspected (to a satisfactory degree) without spinning the bottle because the injected acoustic wave travels round. But the bottle may be spun while it is in the inspection position so that the acoustic pulse is injected at different location around the periphery of the bottle mount, and hence the bottle mouth is examined more uniformly.

By doing so, injection and detection of the acoustic signal are repeated several times. The circuit of FIG. 6 will operate to find the bottle rejectable if the defect is recognized even once. But the arrangement may alternatively be such that the bottle is found rejectable if the defect is recognized at least a predetermined number of times out of the given repeated injections, or the defect is recognized at least a predetermined number of times consecutively.

PULSE ECHO INSPECTION

Figure 7:
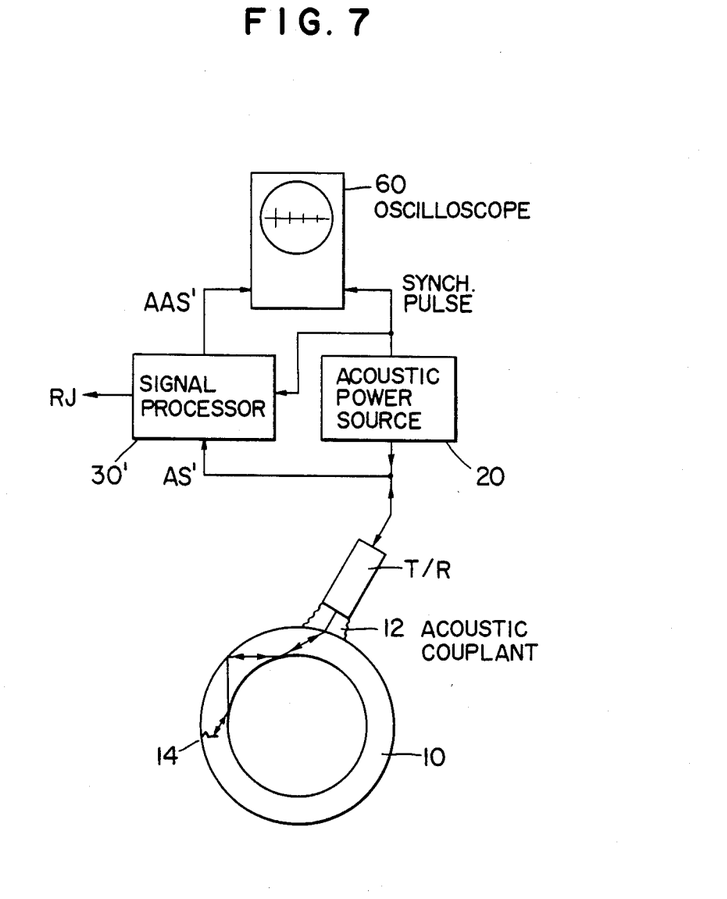
FIG. 7 is a schematic diagram showing an example of arrangement for pulse echo inspection.

The basic elements of an acoustic pulse echo inspection system, which forms another embodiment of the invention, are illustrated in FIG. 7. In this embodiment a single acoustic transducer T/R performs the duties of both acoustic source T and detector R. The acoustic power source 20 applies a pulse to the transducer T/R which generates the acoustic pulse that is coupled into a container 10. This acoustic pulse propagates through the coupling medium 12 and around the wall 10 of the container. The receiver electronics of a signal processor 30' is designed with overload protection which prevents the source pulse from damaging the interfacing electronics while maintaining the high gain necessary to detect the small amplitude, acoustic echoes. A defect 14 in the container will reflect some of the acoustic energy back to the transducer T/R where it is detected. These reflected signals are delayed in time with respect to the source pulse which makes it possible to use time-delayed gates to eliminate potential signal interference from the container surface.

Figure 8:
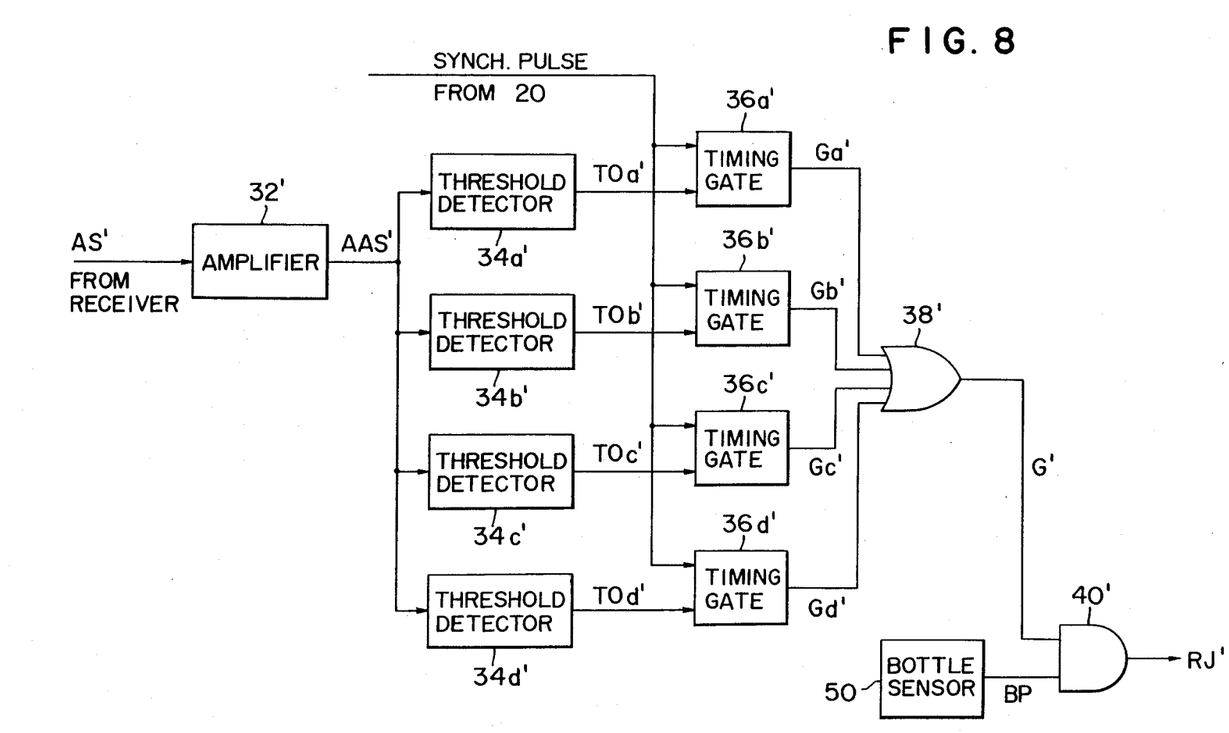
FIG. 8 is a block diagram showing an example of a signal processer 30' of FIG. 7.

FIG. 8 shows an example of the signal processor 30' usable in the system of FIG. 7.

An amplifier 32' amplifies the acoustic signal AS' from the transmitter/receiver to produce an amplified acoustic signal AAS'.

Figure 9:
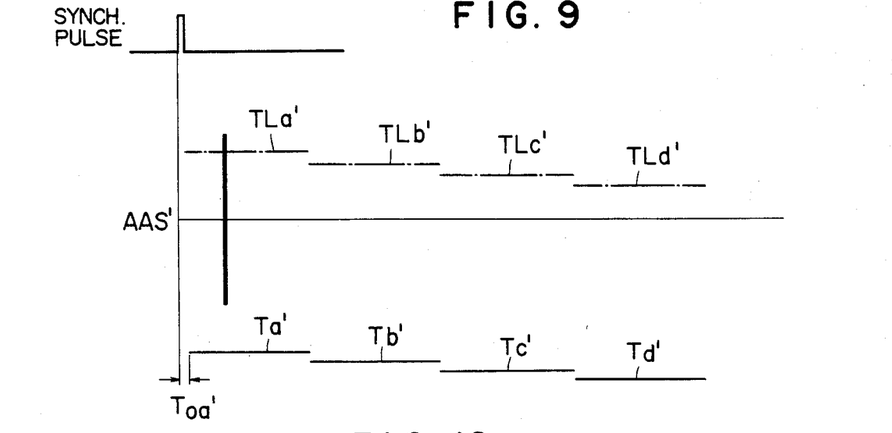
FIG. 9 is a diagram showing the threshold levels of the respective threshold detectors $34a'-34d'$ and the time intervals of the respective timing gates $36a'-36d'$.

Timing gates 36a'-36d' are provided to receive the synchronous pulse from the acoustic power source 20 (FIG. 7) and to open upon expiration of respective predetermined time periods from the reception of the synchronous pulse produced in synchronism with the injection of the acoustic wave pulse and are kept open for respective time intervals $T_a'$, $T_b'$, $T_c'$, $T_d'$ shown in FIG. 9. The time intervals $T_a'$-$T_d'$ are so chosen that the pulses reflected at any defect during the first to fourth round trips would be received by the receiver within the respective time intervals $T_a'$-$T_d'$. More specifically the beginnings of the respective time intervals $T_a'$-$T_d'$ are time points at which the pulse reflected at the beginnings of the first to fourth round trips would be received while the ends of the respective time intervals $T_a'$-$T_d'$ are time points at which the pulse reflected at the ends of the first to fourth round trips would be received.

However, to be more exact, there is a certain blank time $T_{oa}'$ during which no timing gates are open. Such a blank time is provided to disregard reception of any pulse transferred directly from the acoustic power source 20 or reflected at the interface between the acoustic couplant and the container.

Threshold detectors 34a'-34d' are provided in association with the respective timing gates 36a'- 36d', and receive the amplified acoustic signal AAS'. The outputs $TO_a'$-$TO_d'$ of the threshold detectors 34a'-34d' are at "high" or logical "1" level when the signal AAS' is above the respective predetermined threshold levels $TL_a'$-$TL_d'$ (FIG. 9). The threshold levels $TL_a'$-$TL_d'$ of the respective threshold detectors 34a'-34d' are so chosen that the pulses which would appear if the reflection at any defect occurs during the first to the fourth round trips would exceed the respective threshold levels. The longer the acoustic wave travels before it is reflected at a deflect, the smaller the magnitude of the acoustic wave is when it is received by the receiver. The magnitude of the acoustic wave is gradually decreased with the increasing distance of travel. Accordingly, the threshold levels $TL_a'$-$TL_d'$ of the threshold detectors associated with the timing gates which open later have smaller values.

When the output $TO_a'$-$TO_b'$ of the threshold detector 34a'-34d' is "1" while the associated timing gate 36a'-36d' is open, the output $G_a'$-$G_d'$ of the associated timing gate 36a'-36d' becomes at "1".

An OR gate 38' is provided to receive the outputs $G_a'$-$G_d'$ of the timing gates 36a'-36d', and an AND gate 40' is provided to receive the output G' of the OR gate and a bottle present signal BP from the bottle sensor 50.

The output $G_a'-G_d'$ of "1" will pass the OR gate 38', and will pass the AND gate 40' provided that the AND gate 40' is opened by the bottle present signal BP to render the reject signal RJ' "1" thereby indicating that the bottle in the inspection position has a deflect.

Figure 10:
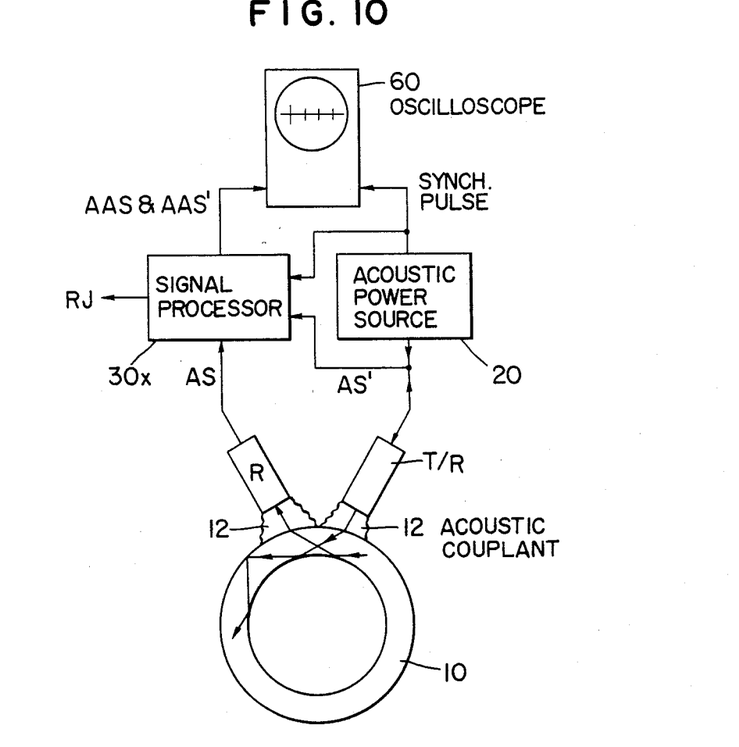
FIG. 10 is a schematic diagram showing an example of arrangement for simultaneous through transmission and pulse echo inspection.

Instead of utilizing either one of the through transmission inspection technique and the pulse echo inspection technique, both techniques may be combined to further improve the reliability of the inspection. This can be accomplished by employing a transmitter/receiver as well as a separate receiver, as shown in FIG. 10, and transferring the both outputs to a signal processor 30x. The signal processor 30x may comprise the amplifier 32, the threshold detectors 34a–34d, the timing gates 36a–36d, and the OR gate 38 of FIG. 6, as well as the amplifier 32', the threshold detectors 34a'–34d', the timing gates 36a'–36d' and the OR gate 38' of FIG. 8. It may also comprise logical elements shown in FIG. 11, namely, an OR gate 42 receiving the outputs G and G' of the OR gates 38 and 38' and an AND gate 40x receiving the output Gx of the OR gate 42 and the bottle present signal BP. In such a case, if a defect is recognized either by through transmission technique or the pulse echo transmission technique, a defect is recognized by the overall arrangement.

Figure 11:
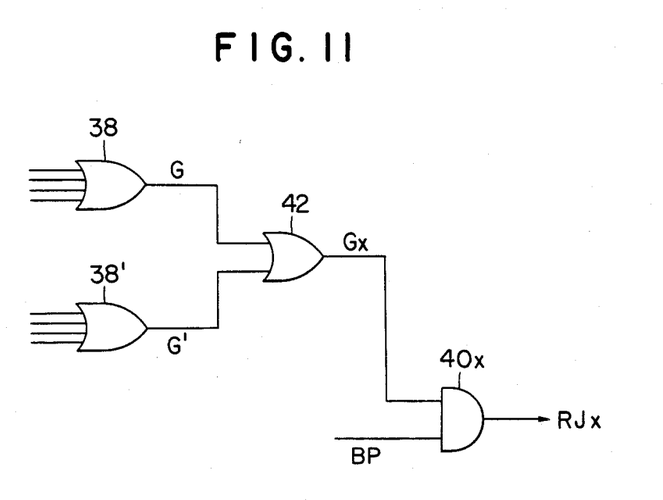
FIGS. 11 and 12 are block diagrams showing examples of circuit for combining the results of the judgement in the through transmission inspection and the pulse echo inspection.
Figure 12:
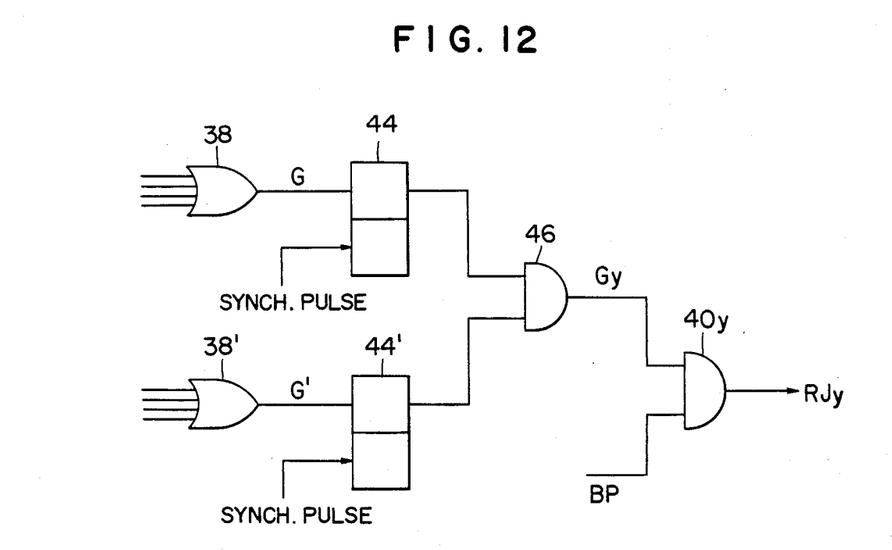

The signal processor 30x may comprise, as an alternative to the circuitry of FIG. 11, a circuitry shown in FIG. 12, namely an SR type flip-flop 44 set by the output G of the OR gate 38, an SR type flip-flop 44' set by the output G' of the OR gate 38', an AND gate 46 receiving the outputs of the flip-flops 44 and 44', and an AND gate 40y receiving the output Gy of the AND gate 46 and the bottle present signal BP. The flip-flops 44 and 44' are reset by the synchronous pulse. With this arrangement, a reject signal is produced when a defect is recognized both by the through transmission inspection technique and the pulse echo inspection technique.

In the embodiments described, a plurality of threshold detectors 34a–34d or 34a'–34d' having different threshold levels are combined with the timing gates 36a–36d or 36a'–36d' which open at different times, and such combination is used to cope with the acoustic signals whose magnitude is reduced with time or distance of travel. Another approach is to use a signal amplifier with a time dependent gain (or a coefficient multiplier with a time dependent coefficient) which increases as a function of time after the synchronous pulse has triggered it. Still another approach is to use a single threshold detector whose threshold level is decreased with time.

BEVERAGE BOTTLE HANDLING

Figure 13:
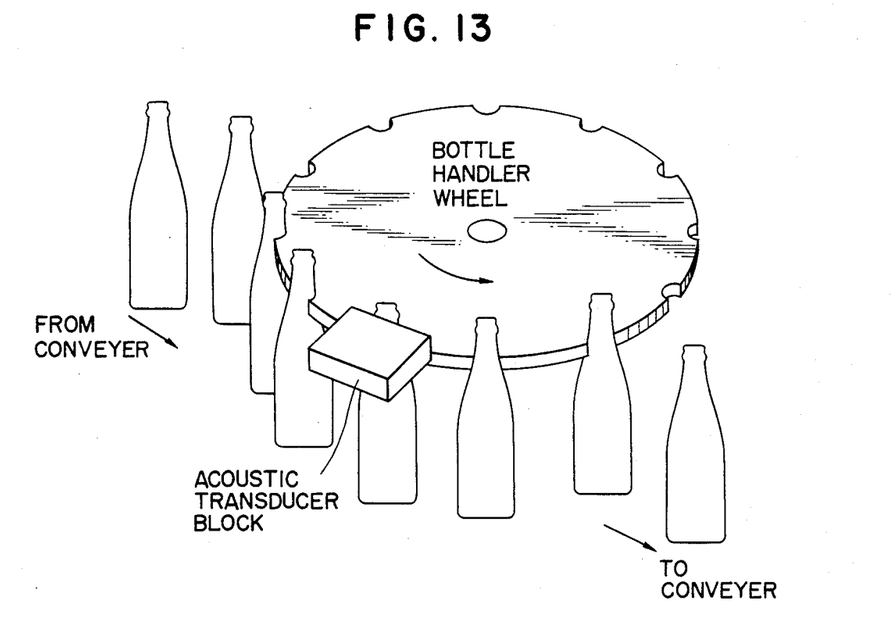
FIGS. 13 and 14 are schematic diagrams showing examples of arrangements for handling bottles for inspection.

One of the best applications of acoustic based inspection is the detection of cracks in recycled and new beverage bottles. As stated earlier, bottle cracks are essentially planar and have no thickness dimension. When they are viewed on edge, they are almost impossible to visually detect. An example of acoustic inspection interfaced with a conventional bottle handling wheel is illustrated in FIG. 13. With this bottle handler, the incoming bottles (from a conveyor) are segregated and held against the large notch in the handling star wheel. This wheel also provides a vertical support for the bottles so that the bottle will move past the transducer head in a very predictable and repeatable manner. The handler wheel can be either driven by bottle pressure from the conveyor line or by a separate motor drive. The transducer block is positioned to inject (and detect) sound at the bottle region of interest. In FIG. 13, the crown support ring of the bottle is being inspected. Other areas may also be similarly inspected, provided there is enough acoustic power to assure a detectable acoustic pulse after one or two revolutions in the container wall and that the signal processor has been set up to receive all potential accept signal conditions (or reject signals in the case of a pulse echo acoustic inspection).

Figure 14:
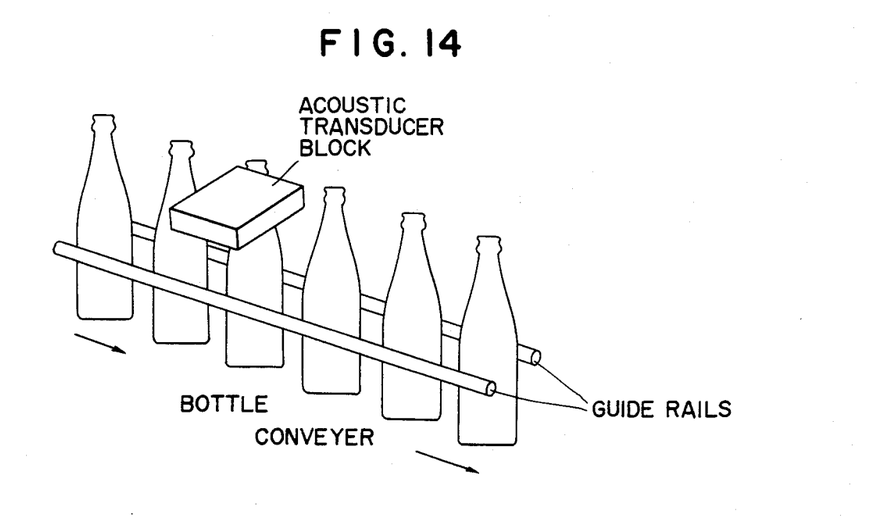

In FIG. 14, a second potential arrangement shows the bottles moving past the transducer block in a linear motion. The conveyor belts and rails would be positioned to produce a repeatable bottle position in front of the transducer block. The position of the bottle at the inspection station (in front of the transducer block) is a key element in a reliable container inspection response.

For both of these arrangements, a bottle sensor 50, shown in FIG. 6, (an optical source/receiver pair where the bottle breaks the optical path between the source and receiver) would enable the signal processing electronics when a bottle is precisely in the correct position in the inspection station. Other hardware embodiments are possible, but the above two include the two most common bottle handling forms (linear and rotary systems).

ACOUSTIC TRANSDUCER BLOCK

Figure 15A:
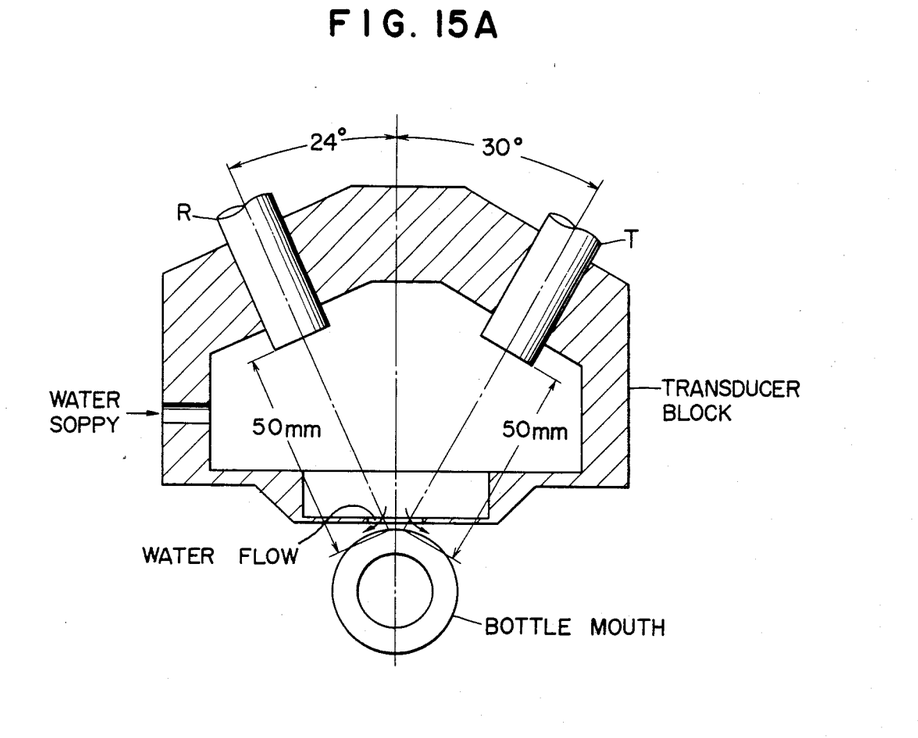
FIGS. 15A and 15B are a cross sectional view and a vertical sectional view showing an example of transducer block.
Figure 15B:
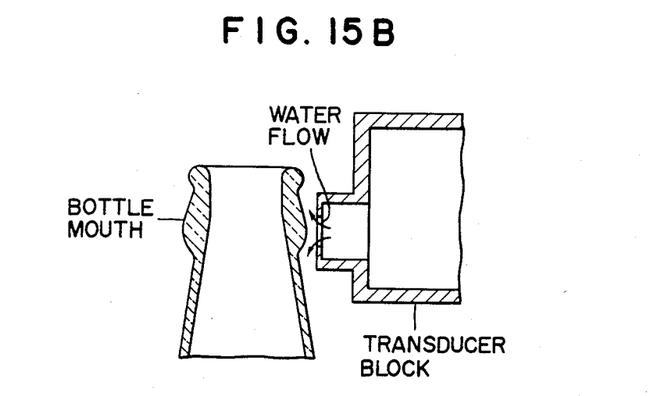

There are also several ways acoustic transducers can be integrated together to perform through transmission and pulse echo inspection. One successfully tested concept illustrated in FIGS. 15A and 15B uses low pressure water to couple acoustic energy in and out of the bottle glass. The water flow is adjusted to prevent air bubbles from entering the water chamber and also to assure good wetting of the bottle surfaces. In this arrangement, the transducers are shown in a through transmission operation mode where one transducer is the acoustic transmitter and the other the acoustic receiver. The dimensions on the transducer block provide a satisfactory acoustic coupling in and out of the crown support ring of a standard crown top bottle. Both transducers are positioned with their focal point on the wall of the bottle. Planar field transducers can also be used but the focused field transducer will provide a stronger acoustic response. Moreover, use of a transducer having an extended focal zone such as an "AXICON" transducer, has been found effective in minimizing the probability of missing a defect, particularly a shallow crack.

This transducer block can also be used for pulse echo inspection by alternately coupling each transducer to a pulse echo electronic circuit (see FIG. 8). The transducers would be pulsed alternately to eliminate potential cross-talk between transducer system.

With this transducer block, it is also possible to simultaneously operate in a through transmission mode and pulse echo mode. A pulsed transducer would listen for its own echo (pulse echo mode) while the other transducers would listen for the through transmission signal. Either of the interfacing circuits as explained with reference to FIGS. 11 and 12 with additional switching electronics could be used in conjunction with the transducer block for such simultaneous operation. The inspection response would be improved if each transducer was independently operated in a pulse-echo mode. This would provide more than 100% coverage of this bottle area and produce a more reliable inspection response.

The use of a liquid couplant (such as water) is preferrable for the coupling of the acoustic energy between the acoustic source transducer and container surface. This couplant media could also be a compliant solid material (such as silicon rubber) or highly viscous material (such as grease) which have low acoustic attenuation. The coupling material should have good impedance matching properties for both the transducer and the container and have a low attenuation at the frequency of the acoustic energy pulse. Based on the above illustrations, other potential embodiments of these acoustic principles should be obvious to those skilled in the art of acoustic and electronic principles.

The invention has been described as being applied to inspection a particular zone of a bottle mouth as indicated in FIG. 4. But the invention is also applicable to inspection of a lip portion Z' (FIG. 4) of the bottle mouth. The zone to be inspected need not be annular, but may be of any other configuration as long as it forms a closed path for the propagation of an acoustic wave pulse (enabling the acoustic wave pulse to circulate along the closed path).

As has been described, the invention provides a unique method and system for detecting a defect in a glass bottle. The invention has particular advantages when used for small diameter cylindrical portion, such as a bottle mouth. This is because the length of the closed path for the acoustic wave is relatively short so that the acoustic wave can make several round trips before it diminishes. Therefore, the chance of a small defect being missed by the acoustic wave during all or most of its round trips is minimal making the inspection more reliable.

What is claimed is:

1. A system for inspecting a glass bottle comprising:
   means for injecting a pulse of acoustic wave into a portion of the glass bottle forming a closed path with the propagation of the acoustic wave pulse so that the injected acoustic wave pulse travels around the closed path,
   means for detecting the acoustic wave pulse while the acoustic wave pulse is traveling around the closed path,
   means for producing a synchronous signal in synchronism with said injection of the acoustic wave pulse,
   means for judging whether there is defect along the closed path in accordance with the magnitude of the detected acoustic wave pulse, said judging means comprising:
   first comparison means for comparing the magnitude of the detected acoustic wave pulse with a threshold level which decreases with time and producing a first signal if the acoustic wave pulse is not found to have exceeding the threshold level during at least one of time intervals set to cover time points when the acoustic wave pulse is normally expected to be detected, said comparison means comprising:
   a plurality of threshold detectors, each receiving the detected acoustic wave pulse and comparing the detected acoustic wave pulse with a threshold level determining for the respective threshold detector, and
   a plurality of timing gate means associated with the respective threshold detectors, each timing gate means defining a respective one of said time intervals responsive to the synchronous signal, and being connected with the associated threshold detector to produce a signal if the associated threshold detector does not find the detected acoustic wave pulse to have exceeded the threshold during the defined time interval, the last mentioned signal constituting said signal produced by said comparison means, and
   means for recognizing the presence of a defect in accordance with said signal produced by said comparison means,
   said portion of the glass bottle forming a closed path comprising a bottle mouth portion having a convexity on its radially outward surface, said injection and said detection of the acoustic wave pulse being made at the top of the convexity.

2. A system of claim 1, further comprising:
   second detecting means for detecting an acoustic wave pulse caused by reflection at any defect which may be present along the closed path,
   wherein said judging means makes said judgement also in accordance with the magnitude of the detected reflected acoustic wave pulse.

3. A system of claim 2, wherein said judging means further comprises:
   second comparison means for comparing the magnitude of the reflected acoustic wave pulse with a threshold level which decreases with time and producing a second signal if the reflected acoustic wave pulse is found to exceed the threshold level, and
   means for recognizing presence of a defect in accordance with said first signal and said second signal.

4. A system of claim 2, wherein an electroacoustic transducer is provided to serve both as said injecting means and said means for detecting the reflected acoustic wave pulse.

* * * * *